US008618157B2

(12) United States Patent  
Mooney et al.

(10) Patent No.: US 8,618,157 B2
(45) Date of Patent: Dec. 31, 2013

(54) PHARMACEUTICAL FORMULATION

(75) Inventors: Brett Antony Mooney, Mt. Ommaney (AU); Panagiotis Keramidas, Carindale (AU)

(73) Assignee: Alphapharm Pty. Ltd., Queensland (AU)

( * ) Notice: Subject to any disclaimer, the term of this patent is extended or adjusted under 35 U.S.C. 154(b) by 104 days.

(21) Appl. No.: 13/000,291

(22) PCT Filed: Feb. 4, 2009

(86) PCT No.: PCT/AU2009/000132
§ 371 (c)(1), (2), (4) Date: Mar. 17, 2011

(87) PCT Pub. No.: WO2009/152551
PCT Pub. Date: Dec. 23, 2009

(65) Prior Publication Data
US 2011/0184039 A1    Jul. 28, 2011

(30) Foreign Application Priority Data

Jun. 20, 2008 (AU) ................................ 2008903115

(51) Int. Cl.
*A61K 31/405* (2006.01)
(52) U.S. Cl.
USPC ............................ 514/415; 514/772; 514/781
(58) Field of Classification Search
USPC .......................................... 514/415, 772, 781
See application file for complete search history.

(56) References Cited

U.S. PATENT DOCUMENTS

| | | | |
|---|---|---|---|
| 4,493,830 A | 1/1985 | Sicuteri | |
| 4,532,244 A | 7/1985 | Innes | |
| 4,816,470 A | 3/1989 | Dowle et al. | |
| 5,307,845 A | 5/1994 | Vanrobaeys et al. | |
| 5,307,953 A | 5/1994 | Regan | |
| 5,480,650 A | 1/1996 | Marchi et al. | |
| 5,554,639 A | 9/1996 | Craig et al. | |
| 5,637,320 A | 6/1997 | Bourke et al. | |
| 5,705,520 A | 1/1998 | Craig et al. | |
| 5,872,145 A | 2/1999 | Plachetka | |
| 6,060,499 A * | 5/2000 | Plachetka | 514/415 |
| 6,365,184 B1 | 4/2002 | Depui et al. | |
| 6,368,627 B1 | 4/2002 | Phillips et al. | |
| 6,384,034 B2 | 5/2002 | Simitchieva et al. | |
| 6,387,410 B1 | 5/2002 | Woolfe et al. | |
| 7,332,183 B2 * | 2/2008 | Plachetka et al. | 424/472 |
| 2002/0099059 A1 | 7/2002 | Saper | |

FOREIGN PATENT DOCUMENTS

| | | |
|---|---|---|
| EP | 1 051 993 | 11/2000 |
| EP | 1 051 995 | 11/2000 |
| EP | 1 064 948 | 1/2001 |
| EP | 1 064 966 | 1/2001 |
| EP | 1 064 967 | 1/2001 |
| WO | WO 00/06161 | 2/2000 |
| WO | WO 2004/060355 | 7/2004 |
| WO | WO 2004/110492 | 12/2004 |
| WO | WO 2007/103113 | 9/2007 |
| WO | WO 2008/124081 | 10/2008 |
| WO | WO 2009/152551 | 12/2009 |

OTHER PUBLICATIONS

Evans et al. CAS: 128: 30231, 1997.*
Bansal et al., "Effect of Formulation and Process Variables on the Dissolution Profile of Naproxen Sodium from Tablets," Drug Development and Industrial Pharmacy. vol. 20, No. 13 pp. 2151-2156 (1994).
Brandes et al., "Sumatriptan-Naproxen for Acute Treatment of Migraine: A Randomized Trial," JAMA. vol. 297, No. 13 pp. 1443-1454 (2007).
Cleves, C., and Tepper, S.J., "Sumatriptan/naproxen sodium combination for the treatment of migraine," Expert Reviews: Neurother. vol. 8, No. 9 pp. 1289-1297 (2008).
International Preliminary Report on Patentability corresponding to International Patent Application No. PCT/AU2009/000132 dated Dec. 21, 2010.
International Search Report corresponding to International Patent Application No. PCT/AU2009/000132 dated Mar. 31, 2009.
Landy et al., "Two Double-Blind, Multicenter, Randomized, Placebo-Controlled, Single-Dose Studies of Sumatriptan/Naproxen Sodium in the Acute Treatment of Migraine: Function, Productivity and Satisfaction Outcomes," MedGenMed. vol. 9, No. 2 p. 53 (2007).
Saadah, "Abortive Migraine Therapy With Oral Naproxen Sodium Plus Metoclopramide Plus Ergotamine Tartrate With Caffeine," Headache. vol. 32, No. 2 pp. 95-97 (1992).
Smith et al., "Sumatriptan/Naproxen Sodium for Migraine: Efficacy, Heatlh Related Quality of Life and Satisfaction Outcomes," Headache. vol. 47, No. 5 pp. 683-692 (2007).
Winner et al., "Twelve-Month Tolerability and Safety of Sumatriptan-Naproxen Sodium for the Treatment of Acute Migraine," Mayo. Clin. Proc. vol. 82, No. 1 pp. 61-68 (2007).

* cited by examiner

*Primary Examiner* — Rei-tsang Shiao
(74) *Attorney, Agent, or Firm* — Jenkins, Wilson, Taylor & Hunt, P.A.

(57) ABSTRACT

A pharmaceutical composition comprising: a) a 5-HT1 agonist; b) an NSAID; and c) a disintegrant characterised in that the disintegrant comprises between about 15 to about 50% w/w based on the weight of the composition, said composition optionally comprising one or more other pharmaceutically acceptable excipients.

21 Claims, No Drawings

PHARMACEUTICAL FORMULATION

TECHNICAL FIELD

The present invention relates to pharmaceutical compositions comprising a combination of 5-HT1 agonists and pharmaceutically acceptable salts thereof with non-steroidal anti-inflammatory drugs (NSAIDs) and pharmaceutically acceptable salts thereof. The invention is further directed towards a process for the manufacture and use of such a composition.

BACKGROUND ART

5-HT1 agonists are known for their ability to cause vasoconstriction of dilated cranial and basilar arteries. NSAIDs are known for their ability to treat pain. The combination of these two classes of drugs has been used to treat migraine headaches in humans (U.S. Pat. Nos. 7,332,183; 6,060,499; 5,872,145; 6,384,034; U.S. Patent Application No. 2002/0099059; EP 1051993; EP 1064967; EP 1051995; EP 1064966; EP 1064948; and Brandes J L et al (2007), "Sumatriptan-naproxen for acute treatment of migraine: a randomized trial", JAMA 297(13):1443-54).

5-HT1 agonists are generally administered orally, intranasally or parenterally (U.S. Pat. Nos. 4,493,830; 4,532,244; 4,816,470; 5,307,845; 5,307,953; 5,554,639; 5,705,520; 6,368,627; and WO 00/06161).

NSAIDs are generally administered orally, for example as a single or multilayer tablet or coated granule dosage form (U.S. Pat. Nos. 6,365,184; 5,637,320; 5,480,650; and 6,387,410).

U.S. Pat. No 7,332,183 discloses a multilayer tablet for a combination of naproxen or pharmaceutically acceptable salt thereof with a triptan. The composition is formulated so that each drug is contained in separate layers located side-by-side so that each dissolves independently of the other. Thus the formulation is said to overcome difficulties associated with the poor in vivo solubility of NSAIDs in conditions of low pH found in the stomach, specifically that the slow eroding nature of NSAIDs may cause the triptan to become entrapped and thereby delay release of the triptan. The manufacturing process necessary to prepare and maintain the actives in separate layers requires specialised equipment and/or processing techniques. This adds to the time and cost for the manufacture of the product.

Bansal P. et al (1994), Drug Development and Industrial Pharmacy, 20(13), pp. 2151-6 discusses the effect of water and mixing time on a composition comprising naproxen sodium and pharmaceutically acceptable excipients. They disclose that naproxen sodium appears to form a pseudopolymorph when granulated in the presence of water affecting the dissolution time of the resultant composition. The effect is also emphasised by an increase in the mixing time during wet granulation.

A simplified pharmaceutical composition and dosage form is required whereby the adverse effects of the combination of these classes of drugs and processing limitations are overcome.

SUMMARY OF THE INVENTION

The present inventors have found that compositions combining a 5-HT1 agonist and an NSAID in a single phase may be prepared.

In a first aspect according to the invention there is provided a pharmaceutical composition comprising:
a) a 5-HT1 agonist,
b) an NSAID
c) a disintegrant
characterised in that the disintegrant comprises between about 15% to 50% w/w based on the weight of the composition, said composition optionally comprising one or more pharmaceutically acceptable excipients.

In an embodiment the 5-HT1 agonist is selected from the group consisting of: a triptan, ergotamine, 5-carbox-amidotryptamine, 3-[(N-2-methoxyethyl) pyrrolidine-2R-yl-methyl]-5-(2-oxo-1,3-oxazolidin-4S-ylmethyl)-1H-indole, 5-(2-oxo-1,3-oxazolidin-4S-ylmethyl)-3-(pyrrolidine-2R-yl-methyl-1H-indole, 3-[N-methylpyrrolidine-2R-ylmethyl]-5-(2-oxo-1,3-oxazolidin-4R,S-ylmethyl)-1H-indole or pharmaceutically acceptable salts thereof. Examples of the triptans sumatriptan, eletriptan, rizatriptan, frovatriptan, almotriptan, zolmitriptan, naratriptan or pharmaceutically acceptable salts thereof.

In an embodiment the 5-HT1 agonist is sumatriptan or a pharmaceutically acceptable salt thereof, typically sumatriptan succinate.

The NSAID of the pharmaceutical composition may be selected from acidic NSAIDs, long acting NSAIDs or COX-2 inhibitors.

In an embodiment the NSAID is a long acting NSAID such as naproxen or a pharmaceutically acceptable salt thereof and typically is naproxen sodium.

In a further aspect of the invention, the pharmaceutical composition comprises a 5-HT1 agonist, an NSAID and pharmaceutically acceptable excipients wherein the therapeutically active ingredients are contained in a single phase, and is characterised in that the composition comprises less than 7% water w/v based on the dosage form weight. Preferably the amount of water is between 2 and 3% water w/v based on the dosage form weight.

In a further aspect of the invention there is provided a method for the preparation of the pharmaceutical composition comprising wet granulation to combine the 5-HT1 agonist and the NSAID and drying the composition, whereby the drying process is selected to minimise the formation of fine granulate material during or after drying.

DETAILED DESCRIPTION OF THE INVENTION

The inventors believe that a single phase dosage form can be prepared that allows for each drug to be released independent of the other. Whilst not wanting to be held to any theory, it is believed that the NSAID will not dissolve at the pH level experienced in the stomach. A dosage form containing this class of drug appears to swell under such conditions and not release any discernable amount of drug at low pH levels. This swollen dosage form is understood to then entrap some or all of the 5-HT1 agonist and thereby delay its release.

Surprisingly, it has been found that the use of a very high level of disintegrant can overcome the problems of the prior art. Disintegrant is normally used in the range of between about 5% to 10%. The levels the inventors have found useful in this invention are between about 15% to 50%, preferably about 30% to 40% w/w based on the weight of the composition. The use of such a high level of disintegrant allows for the combined drugs to be intimately admixed or one drug to be coated onto a core containing the other drug without any adverse effect on the stability or release of either drug. The incorporation of a high level of disintegrant into a single phase composition achieves an acceptable degree of disintegration in the stomach such that any swelling on the part of the NSAID does not have an appreciable effect on the dissolution and bioavailability of the 5-HT1 agonist.

The 5-HT1 agonists of the invention is selected from a triptan, ergotamine, 5-carboxamidotryptamine, 3-[(N-2-methoxyethyl) pyrrolidine-2R-ylmethyl]-5-(2-oxo-1,3-oxazolidin-4S-ylmethyl)-1H-indole, 5-(2-oxo-1,3-oxazolidin-4S-ylmethyl)-3-(pyrrolidine-2R-ylmethyl-1H-indole, 3-[N-methylpyrrolidine-2R-ylmethyl]-5-(2-oxo-1,3-oxazolidin-4R,S-ylmethyl)-1H-indole or pharmaceutically acceptable salts thereof. The triptans can be selected from sumatriptan, eletriptan, rizatriptan, frovatriptan, almotriptan, zolmitriptan and naratriptan or pharmaceutically acceptable salts thereof. In an embodiment, the 5-HT1 agonist is sumatriptan and, more particularly, sumatriptan succinate. The triptans should be administered to patients at the dosages known in the art to be effective at relieving pain. This amount for sumatriptan is in the range between 25 and 100 mg.

The NSAIDs of the invention can be selected from acidic NSAIDs with a $pK_a$ value of less than 7.0, long-acting NSAIDs or cyclooxygenase-2 (COX-2) inhibitors. The long-acting NSAIDs can be selected from flurbiprofen, ketoprofen, naproxen, oxaprozin, etodolac, indomethacin, ketorolac, nabumetone, mefenamic acid, piroxicam, lornoxicam, meloxicam, and pharmaceutically acceptable salts thereof. The COX-2 inhibitors can be selected from rofecoxib, celecoxib, valdecoxib, etoricoxib, JTE-522, L-745,337, NS398, and pharmaceutically acceptable salts thereof. In an embodiment the NSAID is naproxen and, more particularly, naproxen sodium.

The disintegrants are preferably selected from those that exhibit a high tendency for wicking of moisture into the dosage form. These disintegrants generally impart a rapid disintegration time on the dosage form such that the dosage form disintegrates in less than 10 min, preferably less than 5 mins and most preferably less than 1-2 mins. Non-limiting examples of such disintegrants include cross-linked polyvinylpyrrolidone, hydroxypropylcellulose, low substituted hydroxypropylcellulose, carboxymethylcellulose calcium, carboxymethylcellulose sodium, sodium starch glycollate, docusate sodium, pregelatinized starch, calcium phosphate, colloidal silicon dioxide, sodium citrate, polyethylene glycol, polyoxyethylene (e.g. Poloxamer®), magnesium carbonate, calcium carbonate, sodium bicarbonate and a mixture of disintegrant with microcrystalline cellulose (e.g.)Avicel®).

The composition of the invention preferably comprises further pharmaceutically acceptable excipients. A person skilled in the art of pharmaceutical formulation would know and understand the need for these other excipients. Examples of other excipients include fillers or diluents, such as microcrystalline cellulose, microfine cellulose, lactose, starch, pregelatinized starch, calcium carbonate, calcium sulphate, dextrin, dextrates, dextrose, dibasic calcium phosphate dihydrate, tribasic calcium phosphate, kaolin, magnesium carbonate, magnesium oxide, talc, sugar, maltodextrin, mannitol, polymethacrylates (e.g. Eudragit®), potassium chloride, powdered cellulose, sodium chloride, sorbitol or combinations thereof; lubricants, such as magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl dihydrogen phosphate, stearic acid, talc, zinc stearate or combinations thereof; binders, such as acacia, alginic acid, carbomer (e.g. Carbopol®), dextrin, gelatin, carboxymethylcellulose sodium, ethyl cellulose, guar gum, hydrogenated vegetable oil, hydroxyethyl cellulose, hydroxypropyl cellulose (e.g. Klucel®), hydroxypropyl methylcellulose (e.g. Methocel®), methylcellulose, liquid glucose, magnesium aluminium silicate, maltodextrin, polymethacrylates, povidone (e.g. Kollidon®, Plasdone®), pregelatinized starch, sodium alginate, starch or combinations thereof; glidants, such as colloidal silicon dioxide, magnesium trisilicate, powdered cellulose, starch, talc, tribasic calcium phosphate or combinations thereof; and release-rate controlling polymers, such as cellulosic polymers like HPMC, HPC, HEC, polyvinyl acetate, (meth)acrylic acid polymers and derivatives thereof like the Eudragit® range of polymers, and polyvinyl acetate/polyvinyl pyrrolidone copolymers.

The dosage form of the invention is preferably a solid oral dosage form, such as a tablet or a capsule. Tablets can be coated for cosmetic or release-rate controlling purposes. Coating techniques and reasons therefore are well known in the art.

The composition of the invention can be manufactured by techniques well known in the art. These include wet granulation or direct compression. The resulting granules can then be compressed (and optionally coated) or encapsulated.

It has also been found that the level of moisture can have an effect on the quality of the dosage form for the combined product. During the manufacture of compositions according to the invention, it was found that the level of moisture had an adverse effect on the quality of the dosage form. It is believed that certain compounds, for example NSAIDs, have a propensity to absorb water and form complexes. In regard to naproxen sodium, it was observed that water can be absorbed in an amount at least equal to the molar quantity of naproxen. Thus, a naproxen:water ratio of about 1:1 has been observed. When attempting to manufacture a solid oral dosage form with a composition containing high levels of moisture (e.g. greater than about 7%), the composition was then observed to stick to the equipment. Additionally, higher levels of water in the final product can have an adverse effect on the rate of disintegration and the stability of the product.

It was observed by the inventors that the inclusion of moisture in a naproxen sodium composition via a wet granulation technique did not appreciably affect the quality of the dosage form. It was only when sumatriptan succinate was added to the naproxen granules containing higher levels of moisture that these adverse effects were seen. Thus, it is believed that a complex was being formed between naproxen sodium, water and sumatriptan succinate. This complex then exhibited poor dosage form quality and an increase in manufacturing problems.

Thus, the inventors have found that the optimum moisture content of the composition needs to be controlled to between 2 and 3% in the granules prior to compression or encapsulation. This control can be achieved by techniques such as controlling the amount of water entering the composition included with the drugs and excipients, and/or drying the composition to remove excess moisture. The level of moisture during and/or at the finish of manufacture can be determined by well known techniques such Karl Fischer titration and Loss on Drying calculations. These water removal techniques and analysis methods are known in the art.

Additionally, it has been found that if the drying process utilised after granulation produces a higher proportion of fine granules, such as by using a fluid bed dryer ('FBD'), the disintegration time increases. It is thought that the low solubility of naproxen sodium at low pH is acting to block the pores of the solid dosage form produced when a higher proportion of finer granules of the naproxen sodium is present after drying. These smaller granules inhibit the movement of moisture into and through the dosage form and thereby impede the uptake of moisture into the dosage form. This results in a decrease in the amount of moisture available to activate the disintegrant and ultimately an increase of disintegration time which may have an effect on the bioavailability of the sumatriptan succinate.

It has been found, by non-limiting example, that conventional oven drying produces a super-dried granule with a lower proportion of fine granules. These super-dried granules have a higher affinity for moisture uptake. Tablets made from these super-dried granules have been observed to disintegrate in less than two minutes compared to approximately eight minutes for tablets made with granules dried by FBD. Without wishing to be held to any theory, the inventors believe that the finer particles may fill the pores of the dosage form when compressed or encapsulated. As naproxen sodium is not soluble in acidic environments but absorbs moisture and swells, it is believed that the naproxen sodium in the finer particles is swelling within the pores of the dosage form cores and inhibiting further absorption of moisture. This effect is enhanced by the more anhydrous nature of the granules after drying. This moisture is required to activate the disintegrant and thereby, any reduction of availability of moisture impedes the disintegration of the core giving longer disintegration times.

The inventors have found that a composition comprising naproxen sodium, sumatriptan succinate, Crospovidone, magnesium stearate, polyvinylpyrrolidone, anhydrous colloidal silica and water prepared by a wet granulation technique to be particularly advantageous.

EXAMPLES

Example 1

| Ingredient | Amount/Dose (mg) |
| --- | --- |
| Naproxen sodium | 500 |
| Crospovidone | 44 |
| Povidone K30 | 20 |
| Purified water | qs |
| Sumatriptan succinate | 119 |
| Crospovidone | 350 |
| Colloidal silica anhydrous | 6 |
| Magnesium stearate | 22 |
| Opadry White | ~32 |

The naproxen sodium, Crospovidone, Povidone K30 and water were wet granulated. The resultant granules were dried until LOD was less than 3.5%. The dried granules were then crushed through a 0.050 G screen and blended with the sumatriptan succinate, Crospovidone, colloidal silica anhydrous and magnesium stearate. The granules were then compressed into tablets and coated.

The disintegration time in water was 5'16". The loss on drying (LOD) result was 2.52% and the tablet hardness was about 12 to 13 kPa. The tablet showed acceptable quality.

The dissolution of sumatriptan after 15 minutes in 0.01N HCl using USP apparatus type II at 50 rpm immediately after manufacture and then after 4 and 8 weeks storage in HDPE container with child resistant cap at 40° C./75% RH, was as follows:

| Time | T0 | 4 wks | 8 wks |
| --- | --- | --- | --- |
| 15 mins | 88 | 84 | 79 |

Example 2

| Ingredient | Amount/Dose (mg) |
| --- | --- |
| Naproxen sodium | 500 |
| Crospovidone | 44 |
| Povidone K30 | 20 |
| Purified water | qs |
| Sumatriptan succinate | 119 |
| Crospovidone | 350 |
| Colloidal silica anhydrous | 6 |
| Magnesium stearate | 22 |
| Opadry White | ~32 |

The naproxen sodium, Crospovidone, Povidone K30 and water were wet granulated. The resultant granules were screened through and then dried in a conventional oven until LOD was less than 3.50. The dried granules were then crushed through a 0.050 G screen and blended with the sumatriptan succinate, Crospovidone, colloidal silica anhydrous and magnesium stearate. The resultant granules were then compressed into tablets and coated.

The disintegration time in water was 2'11". The loss on drying (LOD) result was 3.3% and the tablet hardness was 14 kPa. The tablet showed acceptable quality.

The dissolution of sumatriptan after 15 minutes in 0.01N HCl using USP apparatus type II at 30 rpm at the initial time point in HDPE container with child resistant cap, was as 81%.

Example 3

| Ingredient | Amount/Dose (mg) |
| --- | --- |
| Naproxen sodium | 500 |
| Crospovidone | 50 |
| Povidone K30 | 20 |
| Purified water | qs |
| Sumatriptan succinate | 119 |
| Crospovidone | 450 |
| Colloidal silica anhydrous | 6 |
| Magnesium stearate | 24 |
| Opadry White | ~32 |

The naproxen sodium, Crospovidone, Povidone K30 and water were wet granulated. The resultant granules were dried LOD was less than 3.5. The dried granules were then crushed through a 0.050 G screen and blended with the sumatriptan succinate, Crospovidone, colloidal silica anhydrous and magnesium stearate. The granules were then compressed into tablets and coated.

The disintegration time in water was 7'13". The tablet hardness was about 27 to 29 kPa. The tablet showed acceptable quality.

The dissolution of sumatriptan after 15 minutes in 0.01N HCl using USP apparatus type II at 50 rpm, was 85%.

Example 4

| Ingredient | Amount/Dose (mg) |
| --- | --- |
| Naproxen sodium | 500 |
| Crospovidone | 50 |
| Povidone K30 | 20 |
| Purified water | qs |
| Sumatriptan succinate | 119 |
| Crospovidone | 350 |
| Colloidal silica anhydrous | 6 |
| Magnesium stearate | 22 |
| Opadry White | ~32 |

The naproxen sodium, Crospovidone, Povidone K30 and water were wet granulated. The resultant granules were dried until LOD was less than 3.5%. The dried granules were then crushed through a 0.050 G screen and blended with the sumatriptan succinate, Crospovidone, colloidal silica anhydrous and magnesium stearate. The granules were then compressed into tablets and coated.

The disintegration time in water was 6'13". The tablet hardness was about 16 to 19 kPa. The tablet showed acceptable quality.

The dissolution of sumatriptan after 15 minutes in 0.01N HCl using USP apparatus type II at 50 rpm, was 69%.

Example 5

| Ingredient | Amount/Dose (mg) |
| --- | --- |
| Naproxen sodium | 500 |
| Crospovidone | 50 |
| Povidone K30 | 20 |
| Purified water | qs |
| Sumatriptan succinate | 119 |
| Crospovidone | 250 |
| Colloidal silica anhydrous | 6 |
| Magnesium stearate | 20 |
| Opadry White | ~32 |

The naproxen sodium, Crospovidone, Povidone K30 and water were wet granulated. The resultant granules were dried until LOD was less than 3.5%. The dried granules were then crushed through a 0.050 G screen and blended with the sumatriptan succinate, Crospovidone, colloidal silica anhydrous and magnesium stearate. The granules were then compressed into tablets and coated.

The disintegration time in water was 8'40". The tablet hardness was about 16 to 18 kPa. The tablet showed acceptable quality.

The dissolution of sumatriptan after 15 minutes in 0.01N HCl using USP apparatus type II at 50 rpm, was 68%.

Example 6

| Ingredient | Amount/Dose (mg) |
| --- | --- |
| Naproxen sodium | 500 |
| Crospovidone | 50 |
| Povidone K30 | 20 |
| Purified water | qs |
| Sumatriptan succinate | 119 |
| Crospovidone | 150 |
| Colloidal silica anhydrous | 6 |
| Magnesium stearate | 18 |
| Opadry White | ~32 |

The naproxen sodium, Crospovidone, Povidone K30 and water were wet granulated. The resultant granules were dried until LOD was less than 3.50. The dried granules were then crushed through a 0.050 G screen and blended with the sumatriptan succinate, Crospovidone, colloidal silica anhydrous and magnesium stearate. The granules were then compressed into tablets and coated.

The disintegration time in water was 10'40". The tablet hardness was about 12 to 13 kPa. The tablet showed acceptable quality.

The dissolution of sumatriptan after 15 minutes in 0.01N HCl using USP apparatus type II at 50 rpm, was 40%.

What is claimed is:

1. A pharmaceutical composition comprising:
   a. a 5-HT1 agonist selected from the group consisting of a triptan, ergotamine, 5carboxamidotryptamine, 3-[(N-2-methoxyethyl) pyrrolidine-2R-ylmethyl]-5-(2-oxo-1,3-oxazolidin-4S-ylmethyl)-1H-indole, 5-(2-oxo-1,3-oxazolidin-4S-ylmethyl)-3-(pyrrolidine-2R-ylmethyl-1H-indole, 3-[N-methylpyrrolidine-2R-ylmethyl]-5-(2-oxo-1,3-oxazolidin-4R,S-ylmethyl)-1H-indole, and pharmaceutically acceptable salts thereof;
   b. a non-steroidal anti-inflammatory drug (NSAID) selected from the group consisting of acidic NSAIDs, long acting NSAIDs, and COX-2 inhibitors; and
   c. a disintegrant, wherein the disintegrant is cross-linked polyvinylpyrrolidone, hydroxypropylcellulose, low substituted hydroxypropylcellulose, carboxymethylcellulose calcium, carboxymethylcellulose sodium, sodium starch glycollate, docusate sodium, pregelatinized starch, colloidal silicon dioxide, sodium citrate, polyethylene glycol, polyoxyethylene, magnesium carbonate, calcium carbonate or sodium bicarbonate, wherein the 5-HT1 agonist and the NSAID are present in the pharmaceutical composition in a single phase, the disintegrant comprises between about 15 to about 50% w/w based on the weight of the composition, and said composition optionally comprises one or more other pharmaceutically acceptable excipients.

2. The pharmaceutical composition of claim 1 wherein the triptan is selected from the group consisting of sumatriptan, eletriptan, rizatriptan, frovatriptan, almotriptan, zolmitriptan, naratriptan and pharmaceutically acceptable salts thereof.

3. The pharmaceutical composition of claim 2 wherein the triptan is sumatriptan.

4. The pharmaceutical composition of claim 3 wherein the sumatriptan is sumatriptan succinate.

5. The pharmaceutical composition of claim 1 wherein the NSAID is a long acting NSAID.

6. The pharmaceutical composition of claim 5 wherein the long acting NSAID is naproxen.

7. The pharmaceutical composition of claim 6 wherein the naproxen is naproxen sodium.

8. The pharmaceutical composition of claim 1 wherein the disintegrant is cross-linked polyvinylpyrrolidone.

9. The pharmaceutical composition of claim 1 wherein the amount of disintegrant is between about 30 to about 40% w/w based on the weight of the composition.

10. The pharmaceutical composition of claim 1 wherein the composition comprises less than 7% water w/w based on the weight of the composition.

11. The pharmaceutical composition of claim 10 wherein the composition comprises between 2 and 3% water w/w based on the weight of the composition.

12. A method of treating a patient suffering from a migraine headache by administration of a pharmaceutical composition as claimed in claim 1.

13. A method for the preparation of the pharmaceutical composition as claimed in claim 1 comprising wet granulation to combine the 5-HT1 agonist and the NSAID and drying the composition, whereby the drying process is selected to minimise the formation of fine granulate material during or after drying.

14. The method of claim 13 wherein the drying process is conventional oven drying.

15. The pharmaceutical composition of claim 1 wherein the amount of disintegrant is between about 30 to about 50% w/w based on the weight of the composition.

16. The pharmaceutical composition of claim 1 wherein the disintegrant is cross-linked polyvinylpyrrolidone, hydroxypropylcellulose, low substituted hydroxypropylcellulose, carboxymethylcellulose calcium, docusate sodium, pregelatinized starch, sodium citrate, polyethylene glycol, polyoxyethylene, magnesium carbonate, or calcium carbonate.

17. The pharmaceutical composition of claim 1 wherein the disintegrant is cross-linked polyvinylpyrrolidone in an amount of about 30 to about 40% w/w based on the weight of the composition.

18. The pharmaceutical composition of claim 1 wherein the 5-HT1 agonist is sumatriptan succinate and the NSAID is naproxen sodium.

19. The pharmaceutical composition of claim 18 wherein the wherein the disintegrant is cross-linked polyvinylpyrrolidone in an amount of about 30 to about 40% w/w based on the weight of the composition.

20. The method of claim 13 wherein the 5-HT1 agonist is sumatriptan succinate and the NSAID is naproxen sodium.

21. A pharmaceutical composition comprising:
a 5-HT1 agonist, wherein the 5-HT1 agonist is sumatriptan succinate; a non-steroidal anti-inflammatory drug (NSAID), wherein the NSAID is naproxen sodium; and
a disintegrant, wherein the disintegrant is cross-linked polyvinylpyrrolidone, and further wherein the 5-HT1 agonist and the NSAID are present in the pharmaceutical composition in a single phase, the disintegrant comprises between about 30 to about 50% w/w based on the weight of the composition, and the composition optionally comprises one or more other pharmaceutically acceptable excipients.

* * * * *